US008354549B2

(12) United States Patent
Zhang

(10) Patent No.: US 8,354,549 B2
(45) Date of Patent: Jan. 15, 2013

(54) METHOD FOR PREPARING A POLYMER CONJUGATE

(75) Inventor: Wen Zhang, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 587 days.

(21) Appl. No.: 12/515,736

(22) PCT Filed: Nov. 30, 2007

(86) PCT No.: PCT/US2007/024620
§ 371 (c)(1),
(2), (4) Date: Sep. 23, 2009

(87) PCT Pub. No.: WO2008/066902
PCT Pub. Date: Jun. 5, 2008

(65) Prior Publication Data
US 2010/0010194 A1 Jan. 14, 2010

Related U.S. Application Data

(60) Provisional application No. 60/861,995, filed on Nov. 30, 2006, provisional application No. 61/003,163, filed on Nov. 14, 2007.

(51) Int. Cl.
*A61K 31/337* (2006.01)
*C07D 305/14* (2006.01)
(52) U.S. Cl. ........................ 549/510; 514/449
(58) Field of Classification Search .................... None
See application file for complete search history.

(56) References Cited

U.S. PATENT DOCUMENTS

| | | | |
|---|---|---|---|
| 5,216,115 A * | 6/1993 | Kohn et al. ................ 528/176 |
| 5,252,714 A | 10/1993 | Harris et al. | |
| 5,372,807 A | 12/1994 | Poiani et al. | |
| 5,446,090 A | 8/1995 | Harris | |
| 5,614,549 A | 3/1997 | Greenwald et al. | |
| 5,648,506 A | 7/1997 | Desai et al. | |
| 5,681,567 A | 10/1997 | Martinez et al. | |
| 5,840,900 A | 11/1998 | Greenwald et al. | |
| 5,859,022 A | 1/1999 | Hausheer et al. | |
| 5,880,131 A | 3/1999 | Greenwald et al. | |
| 5,932,462 A | 8/1999 | Harris et al. | |
| 5,965,566 A | 10/1999 | Greenwald et al. | |
| 6,011,042 A | 1/2000 | Greenwald et al. | |
| 6,121,451 A | 9/2000 | Henegar et al. | |
| 6,127,355 A | 10/2000 | Greenwald et al. | |
| 6,153,655 A | 11/2000 | Martinez et al. | |
| 6,194,580 B1 | 2/2001 | Greenwald et al. | |
| 6,395,266 B1 | 5/2002 | Martinez et al. | |
| 6,403,569 B1 | 6/2002 | Achterrath | |
| 6,437,025 B1 | 8/2002 | Harris et al. | |
| 6,461,603 B2 | 10/2002 | Bentley et al. | |
| 6,602,498 B2 | 8/2003 | Shen | |
| 6,608,076 B1 | 8/2003 | Greenwald et al. | |
| 7,144,978 B2 | 12/2006 | Huang et al. | |
| 2001/0041172 A1 | 11/2001 | Bentley et al. | |
| 2002/0182172 A1 | 12/2002 | Bentley et al. | |
| 2003/0105275 A1 | 6/2003 | Bentley et al. | |
| 2004/0037802 A1 | 2/2004 | Zhao et al. | |
| 2004/0058981 A1 | 3/2004 | Lai et al. | |
| 2004/0077595 A1 | 4/2004 | Cheng et al. | |
| 2005/0112088 A1 | 5/2005 | Zhao et al. | |

FOREIGN PATENT DOCUMENTS

| | | |
|---|---|---|
| CN | 1283643 A | 2/2001 |
| CN | 1381512 A | 11/2002 |
| EP | 0757049 | 3/1999 |
| EP | 0923566 | 10/2003 |
| WO | 97/33552 | 9/1997 |
| WO | 98/41562 | 9/1998 |
| WO | 99/53951 | 10/1999 |
| WO | 00/64486 | 11/2000 |
| WO | 01/62299 | 8/2001 |
| WO | 01/74402 | 10/2001 |
| WO | 02/08789 | 1/2002 |
| WO | 03/031467 | 4/2003 |
| WO | 03/037384 | 5/2003 |
| WO | 03/037385 | 5/2003 |
| WO | 03/091337 | 6/2003 |
| WO | 2004/078121 | 9/2004 |
| WO | 2005/028539 | 3/2005 |

OTHER PUBLICATIONS

Rejection Decision dated Aug. 24, 2011, corresponding to Chinese Patent Application No. 200780044217.0.
Ali, et al., "Novel Cytotoxic 3'-(tert-Butyl) 3'-Dephenyl Analogs of Paclitaxel and Docetaxel", J. Med. Chem., vol. 38, pp. 3821-3828, (1995).
Astruc, et. al., "Denritic Catalysts and Dendrimers in Catalysis", Chem. Rev., vol. 101, pp. 2991-3023, (2001).
Bouvier, et al., "First enzymatically activated Taxotere prodrugs designed for ADEPT and PMT", Bio. & Med. Chem., vol. 12, pp. 969-977, (2004).
Conover, et al., Camptothecin delivery system: enhanced efficacy and tumor accumulation of camptothecin following its conjugation to polyethylene glycol via glycine linker:, Cancer Chemo. Pharm., vol. 42, No. 5, pp. 407-414, (1998).
Conover, et al., "Camptothecin delivery systems: the utility of amino acid spacers for the conjugation of camptothecin polyethylene glycol to create prodrugs", Anti-Cancer Drug Des., vol. 14, No. 6, pp. 499-506, (1999).
Deka, et al., "Deletion of the Oxetane Ring in Docetaxel Analogues: Synthesis and Biological Evaluation", Org. Lett., vol. 5, No. 26, pp. 5031-5034, (2003).
Greenwald, et al., "Poly(ethylene glycol) Conjugated Drugs and Prodrugs: A Comprehensive Review", Critical Rev. in Therap. Drug Carr. Sys., vol. 17, No. 2, pp, 101-161, (2000).
Kanazawa, et al., "Highly Stereocontrolled and Efficient Preparation of the Protected, Esterification-Ready Docetaxel (Taxotere) Side Chain", J. Org. Chem., vol. 59, pp. 1238-1240, (1994).

(Continued)

*Primary Examiner* — Jeffrey E Russel
(74) *Attorney, Agent, or Firm* — Mark A. Wilson

(57) ABSTRACT

Provided herein is a straightforward and efficient method for covalently attaching a polyethylene glycol polymer to docetaxel. The method involves, among other things, a step of reacting docetaxel with a polyethylene glycol polymer comprising a functional group reactive with a hydroxyl group within docetaxel in the presence of a coupling reagent and DPTS. The result of the reacting step is the formation of a polyethylene glycol-docetaxel conjugate having a single polyethylene glycol covalently attached, via an ester linkage, to the hydroxyl group within docetaxel.

25 Claims, 2 Drawing Sheets

OTHER PUBLICATIONS

Lucatelli, et al., "Synthesis of C-3' Methyl Taxotere (Docetaxel)", J. Org. Chem., vol. 67, pp. 9468-9470, (2002).

Merckle, et al., "Semisynthesis of D-Ring Modified Taxoids: Novel Thia Derivatives of Docetaxel", J. Org. Chem., vol. 66, pp. 5058-5065, (2001).

Miller, et al., "Synthesis of Taxoids with Improved Cytotoxicity and Solubility for Use in Tumor-Specific Delivery", J. Med. Chem., vol. 47, pp. 4802-4805, (2004).

Nikolakakis, et al., "Semi-Synthesis of an O-Glycosylated Docetaxel Analogue", Bioorg. & Med. Chem., vol. 11, pp. 1551-1556, (2003).

Ojima, et al., "Synthesis and Structure-Activity Relationships of New Antitumor Taxoids. Effects of Cyclohexyl Substitution at the C-3' and/or C-2 of Taxotere (Docetaxel)", J. Med. Chem., vol. 37, pp. 2602-2608, (1994).

Omayra, et al, Polyester Dendritic Systems for Drug Delivery Applications: In Vitro and In Vivo Evaluation, Bioconj. Chem., vol. 13, pp. 453-461, (2002).

Querolle, et al., "Synthesis of C2-C3'N-Linked Macrocyclic Taxoids. Novel Docetaxel Analogues with High Tubulin Activity", J. Med. Chem., vol. 47, pp. 5937-5944, (2004).

Querolle, et al., "Synthesis of Novel Macrocyclic Docetaxel Analogues. Influence of Their Macrocyclic Ring Size on Tubulin Activity", J. Med. Chem., vol. 46, pp. 3623-3630, (2003).

Roberts, et al., "Chemistry for Peptide and Protein PEGylation", Adv. Drug Del. Rev., vol. 54, pp. 459-476, (2002).

Slichenmyer, et al., "Taxol: a new and effective anti-cancer drug", Anti-Cancer Drugs, vol. 2, pp. 519-530, (1991).

Tian, et al., "Design and Synthesis of Amphiphilic Poly(Ethylene Glycol) Derivatives as Micellar Drug Delivery Systems", Polymer Preprints, Amer. Chem. Soc., vol. 43, No. 2, (Jan. 1, 2002).

Warnecke, et al., "Maleimide-oligo(ethylene glycol) Derivatives of Captothecin as Albumin-Binding Prodrugs: Synthesis and Antitumor Efficacy", Bioconj. Chem., vol. 14, pp. 377-387, (2003).

Wang, et al "Synthesis and Evaluation of a Star Amphiphilic Block Copolymer from Poly(epsilon-caprolactone) and Poly(ethylene glycol) as a Potential Drug Delivery Carrier", Bioconj. Chem., vol. 16, No. 2, pp. 397-405, (2005).

Yamaguchi, et al., "Synthesis of Taxoids 5. Synthesis and Evaluation of Novel Water-Soluble Prodrugs of a 3'-Despheny1-3'Cyclopropyl Analogue of Docetaxel", Bioorg. & Med. Chem. Lett., vol. 9, pp. 1639-1644, (1999).

Zalipsky, et. al., "Attachment of Drugs to Polyethylene Glycols", Eur. Polm., J., vol. 19, No. 12, pp. 1177-1183, (1983).

Enzon Pharmaceuticals, Macromolecular Engineering Technologies, pp. 1-14, (2004).

Nektar—Transforming Therapeutics, Nektar Molecule Engineering: Polyethylene Glycol and Derivatives for Advanced PEGylation, pp. 1-20, (Catalog—2003).

Nektar—Transforming Therapeutic, Nektar Advanced PEGylation: Polyethylene Glycol and Derivatives for Advanced PEGylation, pp. 1-24, (Catalog—2004).

NOF Corporation, PEG Derivatives, Phospholipid and Drug Delivery Materials for Pharmaceuticals, pp. 1-46, (Catalogue 2003—1st).

NOF Corporation, PEG Derivatives, Phospholipid and Drug Delivery Materials for Pharmaceuticals, pp. 1-50, (Catalogue 2003—2nd).

NOF Corporation, PEG Derivatives, Phospholipids and Drug Delivery Materials for Pharmaceutical Products and Formulations, pp. 1-59, (Catalogue Ver. 8—Apr. 2006).

Polypure, Products; PEG amines; PEG acids and amino acids; PEG thiols and disulfides; BIOTINS, (Apr. 2004).

Polypure, Products; PEG amines; PEG acids and amino acids; PEG thiols and disulfides; BIOTINS, (Apr. 2005).

Quanta Biodesign, Labeling, Derivatization and Crosslinking Reagents for Biological and Related Materials with dPEG, pp. 1-38, (Mar. 12, 2004).

Quanta Biodesign, Labeling, Modification and Crosslinking Reagents incorporating our unique monodispersed dPEG Technology, pp. 1-31, (Nov. 5, 2004).

Quanta Biodesign, Ltd., Leading innovator, producer and provider of monodisperse discrete PEG (dPEG) derivatives, (Product Catalog), pp. 1-51, (Updated: Jul. 18, 2005).

Quanta Biodesign, Ltd., Leading innovator, producer and provider of monodisperse discrete PEG (dPEG) derivatives, (Product Catalog), pp. 1-51, (Updated: Nov. 17, 2005).

Shearwater Polymers, Inc., pp. 2-49, (Catalog—Mar. 1995).

Shearwater Polymers, Inc., Polyethylene Glycol and Derivatives, pp. 1-53, (Catalog—Jul. 1997).

Shearwater Polymers, Inc., Polyethylene Glycol and Derivatives: Functionalized Biocompatible Polymers for Research and Pharmaceuticals, pp. 1-50, (Catalog—2000).

Shearwater Corporation, Polyethylene Glycol and Derivatives for Biomedical Applications, pp. 1-17, (Catalog—2001).

PCT International Search Report in PCT Application No. PCT/US2007/024620 mail date Jun. 4, 2009.

PCT International Preliminary Report on Patentability in PCT Application No. PCT/U52007/024620 date of issuance of report Jun. 10, 2009.

Moore, et al., "Room Temperature Polyesterification", Macromolecules, vol. 23, pp. 65-70, (1990).

Chinese Notification of the First Office Action corresponding to Chinese Patent Application No. 200780044217.0 date of notification Jan. 25, 2001.

* cited by examiner

METHOD FOR PREPARING A POLYMER CONJUGATE

CROSS-REFERENCE TO RELATED APPLICATIONS

This application is a 35 U.S.C. §371 application of International Application No. PCT/US2007/024620, filed Nov. 30, 2007, designating the United States, which claims the benefit of priority to U.S. Provisional Application No. 60/861,995, filed Nov. 30, 2006, and to U.S. Provisional Application No. 61/003,163, filed Nov. 14, 2007, the contents of which are incorporated herein by reference in their entirety.

FIELD

The present invention relates generally to a method for covalently attaching one or more water-soluble polymers to an active agent, among other aspects.

BACKGROUND

Over the years, numerous synthetic approaches have been utilized for covalently attaching a water soluble polymer such as a polyethylene glycol to a biologically active agent. Early attempts at PEGylation typically resulted in non-specific covalent attachment of PEG to multiple reactive sites in the active agent, most commonly a polypeptide or protein. In the case of polypeptides, the most common reactive groups for covalent coupling are the alpha or epsilon amino groups of lysine. Early PEGylation chemistry typically employed low molecular weight, linear PEG reagents, and most conjugates were produced via acylation (Roberts, M. J., et al., *Advanced Drug Delivery Reviews*, 54 (2002), 459-476). Such early PEGylated drugs often resulted in poor drug performance, and/or exhibited low batch to batch reproducibility.

Second generation PEGylation chemistry resulted in approaches designed to overcome many of the problems associated with first generation PEGylation reagents—diol contamination, side reactions, unstable linkages, and lack of selectivity in covalent attachment of the polymer to multiple reactive sites in the active agent (Roberts, M. J., et al., ibid). New PEG reagents such as PEG propionaldehyde (U.S. Pat. No. 5,252,714), PEG vinyl sulfone (U.S. Pat. No. 5,446,090) and PEG maleimide (U.S. Pat. No. 6,602,498), among others, were developed and methods involving their use described. Non-linear PEGs such as branched (U.S. Pat. No. 5,932,462) and forked PEGs (U.S. Pat. No. 6,437,025) also became more widely available, e.g., from companies such as Nektar Therapeutics and NOF.

As PEGylation of therapeutics has become more widely employed as one possible approach for improving the pharmacological and other properties of therapeutic agents, the synthetic challenges for consistently forming a well-defined PEGylated therapeutic having beneficial pharmacological properties continue to mount. Such approaches, particular if they are to be adapted to large scale production, should ideally avoid multiple reaction steps, as well as minimize the number of protection, deprotection, and purification steps required, as well as form product in a consistent manner and with reasonably good yields.

SUMMARY OF THE INVENTION

In one aspect, provided herein is a method for covalently attaching a polyethylene glycol polymer to an active agent. The method includes the steps of (i) providing an active agent comprising a first functional group selected from amino, hydroxyl and carboxyl (and activated carboxyl equivalents, e.g., a reactive ester or the like), and (ii) reacting the active agent with a polyethylene glycol comprising a second functional group that is reactive with the first functional group. The reaction is carried out in the presence of a coupling reagent and 4-(dimethylamino)-pyridinium-p-toluenesulfonate (DPTS) under conditions effective to promote reaction between the first and second functional groups, to thereby form a polyethylene glycol-active agent conjugate.

In one embodiment, the coupling agent is a carbodiimide. Representative coupling agents include those selected from the group consisting of dicyclohexylcarbodiimide (DCC), N,N'-diisopropylcarbodiimide (DIC), 1-(3-dimethylaminopropyl)-3-ethylcarbodiimide hydrochloride (EDAC), 1-(3-dimethylaminopropyl)-3-ethylcarbodiimide (EDC), N-tert-butyl-N'-methylcarbodiimide (TBMC), and N-tert-butyl-N'-ethylcarbodiimide (TBEC).

In a preferred embodiment, the coupling reagent is N,N'-diisopropylcarbodiimide.

The reaction is typically carried out in an organic solvent. Suitable solvents include dichloromethane, chloroform, acetonitrile, and tehtrahydrofuran.

In yet a further embodiment, the reaction is carried out at a temperature ranging from 0° C. to 100° C., more preferably, at room temperature.

In still yet another embodiment of the method, the amount of DPTS ranges from about 0.05 to 0.75 equivalents relative to said first functional group, more preferably, from about 0.10 to 0.60 equivalents relative to said first functional group.

In yet an additional embodiment, the amount of the coupling reagent ranges from about 1.25 to 5 equivalents relative to said first functional group.

Preferred second functional groups include amino, hydroxyl, and carboxyl.

Active agents suitable for use in the method include proteins, oligopeptides, polypeptides, small molecules, antibodies, nucleotides, oligonucleotides, and lipids.

In a preferred embodiment of the method, the active agent is a small molecule comprising a first functional group that is hydroxyl or carboxyl. In some instances, the active agent possesses more than one of said first functional groups.

Particularly preferred small molecules include taxanes (e.g., docetaxel or paclitaxel) and camptothecins.

In yet an even more preferred embodiment, the reaction between the first and second functional groups results in formation of an ester bond.

In still an even more particular embodiment, the method results in formation of a docetaxel-polyethylene conjugate having polyethylene glycol covalently attached, via an ester linkgage, to a single hydroxyl site (e.g., the 2' hydroxyl site) on docetaxel.

In the method, the polyethylene glycol may possess any of a number of geometries, e.g., linear, branched, forked, and multi-armed polyethylene glycol. Preferably, the polyethylene glycol is a multi-armed polymer having from about 3 to about 25 arms.

Preferred multi-armed polymers are those comprising a polyol or a polyamine core. Exemplary polyol cores include glycerol, trimethylolpropane, sorbitol, hexaglycerol, and pentaerythritol.

In one embodiment of the method, the polyethylene glycol comprises from about 1 to about 10 of the second functional groups. In an even more specific embodiment, the polyethylene glycol comprises a number of second functional groups selected from 1, 2, 3, 4, 5, and 6. In yet another embodiment, the polyethylene glycol possesses a number of second functional groups selected from 3, 4, and 5.

In yet another embodiment of the method, the active agent comprises more than one first functional group, and the method does not comprise a protection step.

In yet another alternative embodiment of the method, the active agent comprises more than one first functional group (e.g., more than one hydroxyl group), and the method is effective to result in formation of a conjugate having polyethylene glycol covalently attached to only a single site on the active agent.

In yet another embodiment, the method is effective to result in formation of less than about 15% of an N-acyl urea side product, and preferably, less than about 10% of an N-acyl urea side product, and even more preferably, less than about 5% of an N-acyl urea side product.

Each of the herein-described features of the invention is meant to apply equally to each and every embodiment as described herein, unless otherwise indicated.

These and other objects and features of the invention will become more fully apparent when read in conjunction with the following detailed description.

DETAILED DESCRIPTION OF THE INVENTION

Figure 1:
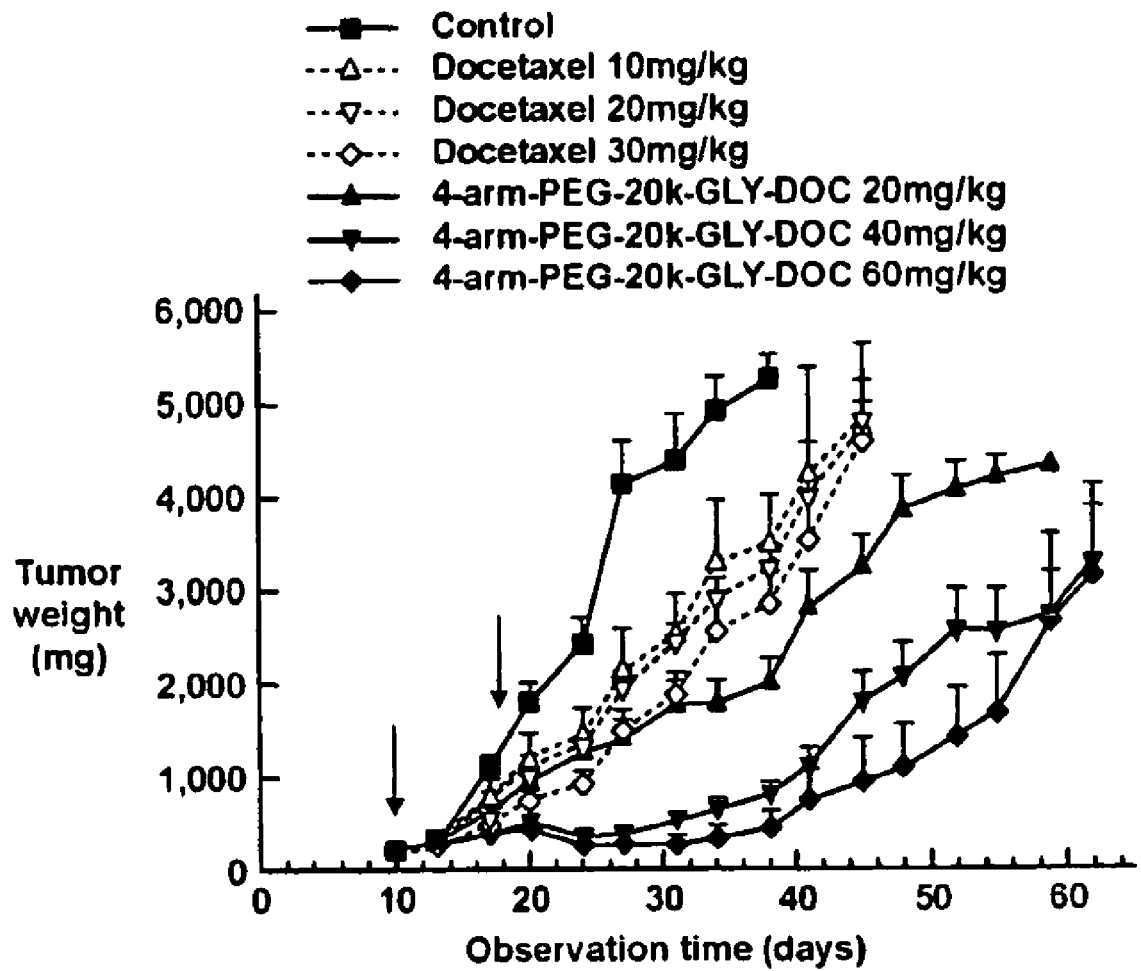
FIG. 1 is a plot demonstrating the effects of two doses of each of three different dosage amounts of docetaxel (10 mg/kg, 20 mg/kg, and 30 mg/kg) and 4-arm-PEG$_{20k}$-glycine-docetaxel, indicated in the figure as "4-arm-PEG-20k-GLY-DOC" (20 mg/kg, 40 mg/kg, and 60 mg/kg) in female xenograft athymic nude mice implanted with H460 non-small cell lung cancer tumors over time as described in Example 3.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

DEFINITIONS

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

A "functional group" is a group that may be used, under normal conditions of organic synthesis, to form a covalent linkage between the structure to which it is attached and another structure, which typically bears a further functional group. The functional group generally includes multiple bond(s) and/or heteroatom(s). Preferred functional groups for use in the polymers and active agents provided herein are described below.

The term "reactive" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive", with reference to a functional group present on a molecule in a reaction mixture, indicates that the group remains largely intact under conditions effective to produce a desired reaction in the reaction mixture.

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include, for example, imidazolyl esters, and benzotriazole esters, and imide esters, such as N-hydroxysuccinimidyl (NHS) esters. An activated derivative may be formed in situ by reaction of a carboxylic acid with one of various reagents, e.g. benzotriazol-1-yloxy tripyrrolidinophosphonium hexafluorophosphate (PyBOP), preferably used in combination with 1-hydroxy benzotriazole (HOBT) or 1-hydroxy-7-azabenzotriazole (HOAT); O-(7-azabenzotriazol-1-yl)-N,N,N',N'-tetramethyluronium hexafluorophosphate (HATU); or bis(2-oxo-3-oxazolidinyl) phosphinic chloride (BOP-Cl).

A "chemical equivalent" of a functional group is one that possesses essentially the same type of reactivity as the functional group. For instance, one functional group that undergoes an SN2 reaction is considered to be a functional equivalent of another such functional group.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups that may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof is meant to encompass protected forms thereof.

"PEG" or "poly(ethylene glycol)" as used herein, is meant to encompass any water-soluble poly(ethylene oxide). Typically, PEGs for use in the present invention will comprise one of the two following structures: "—(CH$_2$CH$_2$O)$_n$—" or "—(CH$_2$CH$_2$O)$_{n-1}$CH$_2$CH$_2$—," depending upon whether or not the terminal oxygen(s) has been displaced, e.g., during a synthetic transformation. The variable (n) is 3 to 3000, and the terminal groups and architecture of the overall PEG may vary. "PEG" means a polymer that contains a majority, that is to say, greater than 50%, of subunits that are —$CH_2CH_2O$—. PEGs for use in the invention include PEGs having a variety of molecular weights, structures or geometries to be described in greater detail below.

"Molecular mass" in the context of a water-soluble polymer of the invention such as PEG, refers to the nominal average molecular mass of a polymer, typically determined by size exclusion chromatography, light scattering techniques, or intrinsic velocity determination in 1,2,4-trichlorobenzene. Molecular weight in the context of a water-soluble polymer, such as PEG, can be expressed as either a number-average molecular weight or a weight-average molecular weight. Unless otherwise indicated, all references to molecular weight herein refer to the weight-average molecular weight. Both molecular weight determinations, number-average and weight-average, can be measured using gel permeation chromatographic or other liquid chromatographic techniques. Other methods for measuring molecular weight values can also be used, such as the use of end-group analysis or the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values such as less than about 1.2, less than about 1.15, less than about 1.10, less than about 1.05, and less than about 1.03. As used herein, references will at times be made to a single water-soluble polymer having either a weight-average molecular weight or number-average molecular weight; such references will be understood to mean that the single-water soluble polymer was obtained from a composition of water-soluble polymers having the stated molecular weight.

The term "linker" is used herein to refer to an atom or a collection of atoms used to link interconnecting moieties, such as an organic radical core and a polymer segment. A linker moiety may be hydrolytically stable or may include a physiologically hydrolyzable or enzymatically degradable linkage.

The term "spacer" is used herein to refer to a collection of atoms used to link interconnecting moieties, such as a polymer segment and an active agent, D. A spacer moiety may be hydrolytically stable or may include a physiologically hydrolyzable or enzymatically degradable linkage.

A "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Illustrative hydrolytically unstable linkages include carboxylate ester, phosphate ester, anhydrides, acetals, ketals, acyloxyalkyl ether, imines, orthoesters, peptides and oligonucleotides.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multi-armed" in reference to the geometry or overall structure of a polymer refers to polymer having 3 or more polymer-containing "arms". Thus, a multi-armed polymer may possess 3 polymer arms, 4 polymer arms, 5 polymer arms, 6 polymer arms, 7 polymer arms, 8 polymer arms or more, depending upon its configuration and core structure. One particular type of highly branched polymer is a dendritic polymer or dendrimer, that, for the purposes of the invention, is considered to possess a structure distinct from that of a multi-armed polymer.

"Branch point" refers to a bifurcation point comprising one or more atoms at which a polymer splits or branches from a linear structure into one or more additional polymer arms. A multi-arm polymer may have one branch point or multiple branch points.

A "dendrimer" is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

"Substantially" or "essentially" means nearly totally or completely, for instance, 95% or greater of some given quantity.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

"Electrophile" refers to an ion, atom, or collection of atoms that may be ionic, having an electrophilic center, i.e., a center that is electron seeking, capable of reacting with a nucleophile.

"Nucleophile" refers to an ion or atom or collection of atoms that may be ionic, having a nucleophilic center, i.e., a center that is seeking an electrophilic center, and capable of reacting with an electrophile.

"Active agent" as used herein includes any agent which provides some pharmacologic, often beneficial, effect that can be demonstrated in-vivo or in vitro. As used herein, these terms further include any physiologically or pharmacologically active substance that produces a localized or systemic effect in a patient.

"Difunctional" or "bifunctional" as used interchangeable herein means an entity such as a polymer having two functional groups contained therein, typically at the polymer termini. When the functional groups are the same, the entity is said to be homodifunctional or homobifunctional. When the functional groups are different, the polymer is said to be heterodifunctional or heterobifunctional.

A basic or acidic reactant described herein includes neutral, charged, and any corresponding salt forms thereof.

The terms "subject", "individual" or "patient" are used interchangeably herein and refer to a vertebrate, preferably a mammal. Mammals include, but are not limited to, murines, rodents, simians, humans, farm animals, sport animals and pets. Such subjects are typically suffering from or prone to a condition that can be prevented or treated by administration of a polymer of the invention, typically but not necessarily in the form of a polymer-active agent conjugate as described herein.

The term "about", particularly in reference to a given quantity, is meant to encompass deviations of plus or minus five percent.

"Optional" or "optionally" means that the subsequently described circumstance may or may not occur, so that the description includes instances where the circumstance occurs and instances where it does not.

A "small molecule" may be defined broadly as an organic, inorganic, or organometallic compound typically having a molecular weight of less than about 1000. Small molecules of the invention encompass oligopeptides and other biomolecules having a molecular weight of less than about 1000.

An "active agent moiety" in reference to a conjugate of the invention, refers to the portion or residue of the unmodified parent active agent up to the covalent linkage resulting from covalent attachment of the drug (or an activated or chemically modified form thereof) to a polymer. Upon hydrolysis of the hydrolyzable linkage between the active agent moiety and the multi-armed polymer, the active agent per se is released.

Overview

Docetaxel (Taxotere®) is a chemotherapeutic agent this is used mainly for the treatment of breast, ovarian, and non-small cell lung cancer (Lyseng-Williamson K A, Fenton, C. *Drugs*, 2005; 65(17): 2513-31). It is a semi-synthetic analoge of paclitaxel, and differs from paclitaxel at two positions in its chemical structure. The main chemical differences between paclitaxel and docetaxel are the substitutions at the 3'-nitrogen on the side chain (BOC vs. benzoyl) and the 10-position of the taxoid core (free alcohol vs. acetate). Both taxoids are associated with a number of undesirable side effects, and their poor water-solubility hampers their clinical application.

In an effort to overcome such disadvantages, various approaches have been described for synthesizing prodrugs and various analogues of paclitaxel. In contrast, significantly fewer studies directed towards modification of docetaxel have been reported, even though docetaxel is more active in both in vitro and in vivo assays than paclitaxel, thereby seeming to make docetaxel a more promising candidate for modification. This discrepancy is presumably due, at least in part, to docetaxel's chemical structure. Docetaxel contains four free hydroxyl groups located at the 1, 7, 10 and 2'-positions. Specifically, the three secondary alcohols at the 7, 10, 2'-positions create considerable challenges when attempting single site modification of the drug, or any drug similarly having multiple reactive groups. Many of the reported derivatives of docetaxel are not prepared directly from the parent compound but from a protected precursor. Such synthetic approaches often involve multi-step reactions and complicated chemical transformations to achieve the required chiral centers. Some researchers have attempted to selectively protect specific hydroxyl groups on docetaxel, but have achieved limited success due to low reaction yields and difficulty in the separation of positional isomers obtained. The synthesis of a modified or drug-delivery enhanced active agent must result in reasonable yields to make any such approach economically attractive.

An effort on the part of the inventors to prepare an exemplary PEG-docetaxel conjugate using conventional dicyclohexylcarbodiimide/dimethylaminopyridine coupling chemistry resulted in formation of a significant quantity of one or more side products—presumably due, at least in part, to the sterically hindered environment of the activating groups on the PEG reagent employed.

In view of the foregoing, the inventors have recognized the immediate need for a straightforward method for preparing PEG conjugates, particularly conjugates of small molecules, wherein such method does not require protection of reactive groups on the small molecule prior to conjugation. Such method is particularly advantageous for small molecules having multiple reactive groups, and is described in detail herein.

Conventional Coupling

Conventional synthetic techniques for preparing a single site polymer-modified active agent from an agent having multiple reactive groups typically involve multi-step reactions requiring multiple selective protection/deprotection steps. Such reactions are often hampered by low yields and difficulty in separation of the desired product(s). In an attempt to avoid use of a protected active agent precursor, the inventors first attempted direct coupling of the exemplary small molecule, docetaxel, to an illustrative multi-armed polymer as described in detail in Example 1A. The structure of docetaxel is shown below, with arrows illustrating the molecule's multiple hydroxyl groups capable of undergoing chemical transformation.

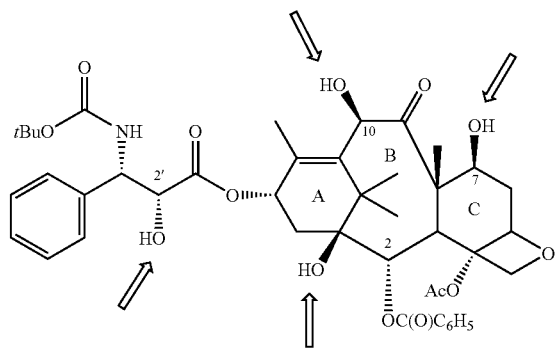

Briefly, a multi-armed PEG reagent, 4-arm-PEG$_{20k}$-glycine, was reacted with docetaxel, utilizing conventional coupling reagents, dicyclohexylcarbodiimide and dimethylaminopyridine (DCC/DMAP). The reaction (i) generated a significant amount of the side product, N-acyl urea, and (ii) was difficult to analyze and purify.

An alternative approach to forming the desired product was also explored in which the candidate small molecule, docetaxel, was first modified with a linker, glycine (Fmoc-glycine), followed by covalent attachment to the PEG reagent (Example 1B). Unfortunately, following purification, the yield of the desired 2'-glycine-modified docetaxel was quite low, approximately 20%, and was accompanied by the formation of several different positional isomers.

Method of Synthesis

To overcome the above-described technical problems, among others, the inventors have developed a coupling reaction for preparing PEG conjugates that suppresses undesired side-reactions and promotes formation of the desired product in good yields and purity, without having to start from an active agent having one or more protecting groups (i.e., utilizes a non-protected starting material).

The synthetic method provided herein utilizes a molecular complex formed by 4-(dimethylamino)pyridine and p-toluenesulfonic acid to effect formation of PEG conjugates in high yields and purities. The synthetic route described herein is effective in supressing undesired side reactions, and the crude product can often be purified by simple precipitation.

In particular, provided herein is a method for covalently attaching a polyethylene glycol polymer to an active agent. The method includes the steps of (i) providing an active agent comprising a first functional group, e.g., selected from amino, hydroxyl, and carboxyl (and activated equivalents thereof), and (ii) reacting the active agent with a polyethylene glycol comprising a second functional group that is reactive with the first functional group. The reaction is carried out in the presence of a coupling reagent and 4-(dimethylamino)-pyridinium-p-toluenesulfonate (DPTS) under conditions effective to promote reaction between the first and second functional groups, to thereby form a polyethylene glycol-active agent conjugate.

Polyethylene Glycol Reagent

The polyethylene glycol reagent may possess any of a number of geometries, e.g., linear, branched, forked, and multi-armed polyethylene glycol. The PEG reagent contains at least one functional group (referred to generally herein as a "second functional group" to distinguish such functional group from one or more functional groups contained in the active agent) suitable for reaction with a functional group on the active agent, to thereby form the desired conjugate. Exemplary functional groups for coupling to an active agent include amino, hydroxyl, and carboxyl, and are intended to encompass activated forms thereof where applicable.

PEG reagents suitable for use include those described in Nektar Advanced PEGylation Catalog, 2005-2006, activated PEGs available from NOF Corporation, and the like.

In one particular embodiment of the method, the polyethylene glycol is a multi-armed polymer having from about 3 to about 25 arms, or more preferably is a multi-armed polymer having a number of arms selected from 3, 4, 5, 6, 7, 8, 9, and 10.

Multi-armed polymers may comprise any of a number of differing polymer cores, such as a polyol or a polyamine core, such as those described in U.S. Patent Application No. 2005/0112088. Preferred polyols forming a multi-arm polymer core, from which one or more PEG arms extend, include glycerol, trimethylolpropane, reducing sugars such as sorbitol or pentaerythritol, and glycerol oligomers, such as hexaglycerol.

Typically, the total number average molecular weight of the polyethylene glycol reagent is about 800 daltons (Da) to about 100,000 Da, more preferably about 10,000 Da to about 60,000 Da, most preferably about 15,000 to about 60,000 Da. Polymers having a number average molecular weight of about 5,000 Da, about 8,000 Da, about 10,000 Da, about 12,000 Da, about 15,000 Da, about 20,000 Da, about 25,000 Da, about 30,000 Da, about 35,000 Da, about 40,000 Da, about 45,000 Da, about 50,000 Da, and about 60,000 Da, among others, are particularly preferred. In the instance there the polymer is a multi-armed polymer, the actual molecular weight of a multi-armed polymer will depend, of course, on the number of polymer arms and the molecular weight of each polymer arm in the overall multi-armed polymer, as well as the degree of polydispersity of the polymer.

Typically, the polyethylene glycol comprises from about 1 to about 10 of the second functional groups. For example, a polyethylene glycol may contain a number of second functional groups selected from 1, 2, 3, 4, 5, and 6.

Illustrative multi-armed polymer reagents, as well as their corresponding conjugates, suitable for use in the present method, are described in U.S. Patent Application No. 2005/0112088.

Preferred multi-armed polymers for use in the method include the following, where the structures below may further comprises an additional linker or functional group connecting one or more PEG arms (ideally each of the PEG arms) to the active agent:

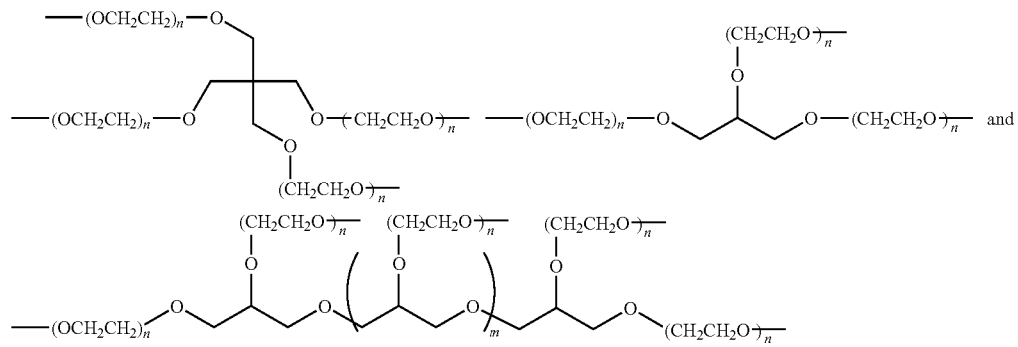

where n typically ranges from about 5 to about 400, and m ranges from 0 to about 5.

One particularly preferred multi-arm reagent is 4-arm-PEG-glycine (structure shown below), although the glycine linker may be replaced by any other suitable linker:

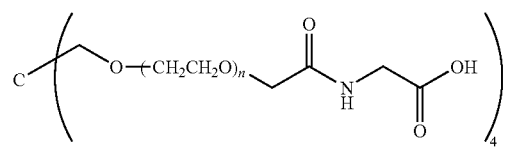

Provided below are illustrative structures corresponding to idealized conjugates that may be formed from the method, assuming that each of the hydroxyls in the parent polyol has been transformed to a polymer arm and that each polymer arm has drug covalently attached thereto. In the illustrative examples below, Q typically corresponds to O, but can equally be considered as corresponding to S, —NH—, or —NH—C(O)—, and POLY corresponds to polyethylene glycol.

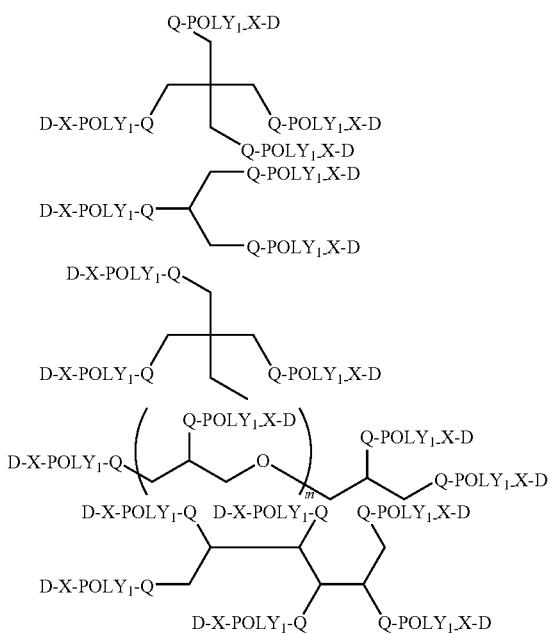

In reference to the foregoing exemplary structures, X represents a spacer that most typically comprises a hydrolyzable linkage, where the hydrolyzable linkage is attached directly to the active agent, D. The overall linkage between the polymer and each drug molecule preferably comprises a hydrolytically degradable portion, such as an ester linkage, so that the active agent is released over time from the multi-armed polymer core. The particular identity of the spacer will depend at least in part upon the particular PEG reagent employed in the method.

Often, at least one atom of the hydrolyzable linkage is contained in the active agent in its unmodified form, such that upon hydrolysis of the hydrolyzable linkage comprised within X, the active agent, D, is released. Generally speaking, the spacer has an atom length of from about 4 atoms to about 50 atoms, or more preferably from about 5 atoms to about 25 atoms, or even more preferably from about 5 atoms to about 20 atoms. Typically, the spacer is of an atom length selected from the group consisting of 4, 5, 6, 7, 8, 9, 10, 11, 12, 13, 14, 15, 16, 17, 18, 19, and 20. When considering atom chain length, only atoms contributing to the overall distance are considered. For example, a spacer having the structure, —$CH_2$—C(O)—NH—$CH_2CH_2$O—$CH_2CH_2$O—C(O)—O— has a chain length of 11 atoms, since substituents are not considered to contribute significantly to the length of the spacer.

Active Agent

Active agents suitable for use in the method include proteins, oligopeptides, polypeptides, small molecules, antibodies, nucleotides, oligonucleotides, and lipids. Preferably, the active agent is a small molecule comprising a first functional group that is either hydroxyl or carboxyl, or any other moiety suitable for covalent attachment to the polyethylene glycol reagent. The active agent may, in certain instances, possess more than one first functional group. The method provided herein is especially advantageous for such active agents.

In a specific embodiment, the active agent moiety is a small molecule possessing a molecular weight of less than about 1000. In yet additional embodiments, the small molecule drug possesses a molecular weight of less than about 800, or even less than about 750. In yet another embodiment, the small molecule drug possesses a molecular weight of less than about 500 or, in some instances, even less than about 300.

Preferred active agent moieties include anticancer agents. Particularly preferred are oncolytics having at least one hydroxyl group.

Particularly preferred small molecules include taxanes (e.g., docetaxel or paclitaxel) and camptothecins.

The term "camptothecin compound" as used herein includes the plant alkaloid 20(S)-camptothecin, as well as pharmaceutically active derivatives, analogues and metabolites thereof. Examples of camptothecin derivatives include, but are not limited to, 9-nitro-20(S)-camptothecin, 9-amino-20(S)-camptothecin, 9-methyl-camptothecin, 9-chloro-camptothecin, 9-fluoro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin (SN38), 10,11-methylenedioxy camptothecin, and 10,11-ethylenedioxy camptothecin, and 7-(4-methylpiperazinomethylene)-10,11-methylenedioxy camptothecin, 7-ethyl-10-(4-(1-piperidino)-1-piperidino)-carbonyloxy-camptothecin, 9-hydroxy-camptothecin, and 11-hydroxy-camptothecin. Particularly preferred camptothecin compounds include camptothecin, irinotecan, and topotecan.

Certain preferred camptothecin compounds correspond to the generalized structure below.

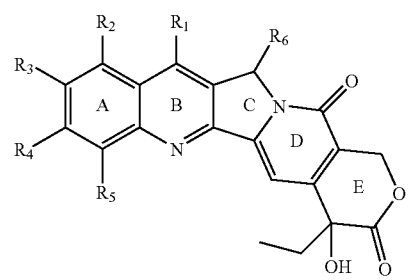

XI wherein $R_1$-$R_5$ are each independently selected from the group consisting of hydrogen; halo; acyl; alkyl (e.g., C1-C6 alkyl); substituted alkyl; alkoxy (e.g., C1-C6 alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxcarbonyl; alkoxycarbonyl; alkylcarbonyloxy; alkylcarbonylamino; carbamoyloxy; arylsulfonyloxy; alkylsulfonyloxy; —C($R_7$)=N—(O)$_i$—$R_8$ wherein $R_7$ is H, alkyl, alkenyl, cycloalkyl, or aryl, i is 0 or 1, and $R_8$ is H, alkyl, alkenyl, cycloalkyl, or heterocycle; and $R_9$C(O)O— wherein $R_9$ is halogen, amino, substituted amino, heterocycle, substituted heterocycle, or $R_{10}$—O—$(CH_2)_m$— where m is an integer of 1-10 and $R_{10}$ is alkyl, phenyl, substituted phenyl, cycloalkyl, substituted cycloalkyl, heterocycle, or substituted heterocycle; or $R_2$ together with $R_3$ or $R_3$ together with $R_4$ form substituted or unsubstituted methylenedioxy, ethylenedioxy, or ethyleneoxy; and $R_6$ is H or OR', wherein R' is alkyl, alkenyl, cycloalkyl, haloalkyl, or hydroxyalkyl.

Exemplary substituting groups include hydroxyl, amino, substituted amino, halo, alkoxy, alkyl, cyano, nitro, hydroxycarbonyl, alkoxycarbonyl, alkylcarbonyloxy, alkylcarbonylamino, aryl (e.g., phenyl), heterocycle, and glycosyl groups.

In one particularly preferred embodiment, D is irinotecan, where the H on the 20-position hydroxyl is absent in the final multi-armed prodrug conjugate.

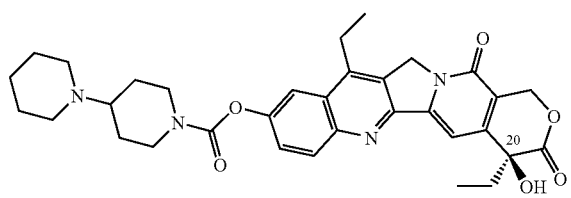 [SMILES: CCc1c2c(nc3ccc(OC(=O)N4CCC(N5CCCCC5)CC4)cc13)-c1cc3c(c(=O)n1C2)COC(=O)[C@]3(O)CC]

In yet another embodiment, D is paclitaxel or docetaxel. One particularly preferred D is docetaxel, where the H at the 2' position is absent in the final multi-armed polymer conjugate:

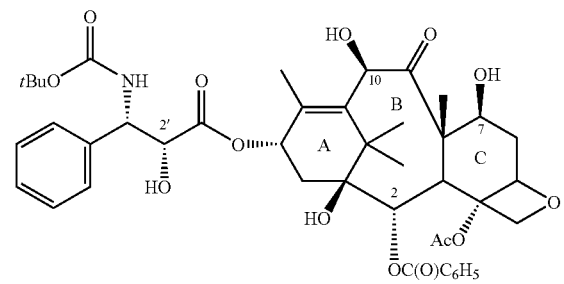

Preferably, an active agent for use in the invention possesses at least one free hydroxyl, carboxyl, thio, amino group, or the like (i.e., "handle") suitable for covalent attachment to the polymer. Preferably, an active agent possesses at least one functional group suitable for forming a hydrolyzable linkage when reacted with a polyethylene glycol reagent, but may possess 2, 3, 4, or more such functional groups. Preferably, the polymer is attached to only one of such functional groups (i.e., is attached at only a single site) in the active agent.

In instances in which a desired point of attachment in a small molecule (or any molecule) is sterically hindered, a single step conjugation reaction may be difficult to accomplish in significant yields. In such instances, either the desired point of attachment in the molecule (e.g., the 2' hydroxyl in docetaxel) or the PEG reagent may be functionalized by reaction with a short linker or spacer moiety. Such an approach is applicable to many small molecules, particularly those having a site of covalent attachment that is inaccessible to an incoming reactive polymer. Preferred linkers for use include t-BOC-glycine or other amino acids having a protected amino group and an available carboxylic acid group (See Zalipsky et al., "Attachment of Drugs to Polyethylene Glycols", Eur. Polym. J., Vol. 19, No. 12, pp. 1177-1183 (1983)). See for example, Examples 1A and 1B herein. Preferred amino acids include alanine, glycine, isoleucine, leucine, phenylalanine, and valine.

Other suitable spacer can also be used in lieu of the amino acids described above.

Coupling Reagent

Preferred coupling agents for use in the present method are carbodiimides. Representative coupling agents include those selected from the group consisting of dicyclohexylcarbodiimide (DCC), N,N'-diisopropylcarbodiimide (DIC), 1-(3-dimethylaminopropyl)-3-ethylcarbodiimide hydrochloride (EDAC), 1-(3-dimethylaminopropyl)-3-ethylcarbodiimide (EDC), N-tert-butyl-N'-methylcarbodiimide (TBMC), N-tert-butyl-N'-ethylcarbodiimide (TBEC), and 1,3-di-para-tolylcarbodiimide, among others. Such coupling agents are available from, e.g., Sigma-Aldrich.

One particularly preferred coupling reagent is N,N'-diisopropylcarbodiimide.

4-(dimethylamino)-pyridinium-β-toluenesulfonate (DPTS)

The coupling reaction is typically conducted in the presence of 4-(dimethylamino)-pyridinium-p-toluenesulfonate, a 1:1 molecular complex formed by 4-(dimethylamino)pyridine and para-toluenesulfonic acid (Jeffrey S. Moore and Samuel I. Stupp, Macromolecules, 1990, 23, 65-70). Preferably, the reagent is freshly prepared prior to use.

The reagent is not hydroscopic, and can be stored for extended periods at room temperature.

Reaction Conditions

The coupling reaction is typically carried out in an organic solvent. Suitable solvents include dichloromethane, chloroform, acetonitrile, and tetrahydrofuran, among others.

Typically, the coupling reaction is carried out at a temperature ranging from about 0° C. to about 100° C. Preferably, the reaction is carried out at room temperature (i.e., absent heating or cooling), and may be accompanied by stirring. Room temperature typically ranges from about 18° C. to about 23° C.

Generally, the amount of DPTS ranges from about 0.05 to about 0.75 equivalents relative to the first functional group (i.e., the desired point of attachment in the active agent), more preferably, from about 0.10 to 0.60 equivalents relative to the first functional group. The amount of the coupling reagent generally ranges from about 1.25 to 5 equivalents relative to the first functional group. Preferred first functional groups are hydroxyl and carboxyl.

Preferred second functional groups (i.e., a reactive group present in the polyethylene glycol reagent) include amino, hydroxyl, and carboxyl, and activated equivalents thereof, where of course, the first and second functional groups are selected to react with each other.

Preferably, the reaction between the first and second functional groups results in formation of an ester bond (for example, resulting from reaction of a carboxylic acid or activated carboxylic acid with the hydroxyl group of an alcohol).

In certain instances, the active agent comprises more than one first functional group, and the method does not comprise (or is absent) a protection step, such that the resulting conjugate product is modified at only a single "first functional group" site.

One notable advantage of the instant method is the minimal formation of an N-acyl urea side product resulting from the carbodiimide coupling agent. Generally, the method is effective to result in formation of less than about 15% of an N-acyl urea side product, and preferably, less than about 10% of an N-acyl urea side product, and even more preferably, less than about 5% of an N-acyl urea side product. See Example 2 in which the synthetic method results in formation of a docetaxel-polyethylene conjugate having polyethylene glycol covalently attached, via an ester linkgage, to a single hydroxyl site (e.g., the 2' hydroxyl site) on docetaxel, absent formation of detectable amounts of an N-acyl urea side product.

Yields of the desired polyethylene glycol-active agent conjugate prepared by the instant method are typically greater than about 70%, preferably greater than about 75%, more preferably greater than about 80%, even more preferably greater than 85%, and most preferably are greater than 90%.

The prodrug product may be further purified. Methods of purification and isolation include precipitation followed by filtration and drying, as well as chromatography. Suitable chromatographic methods include gel filtration chromatography and ion exchange chromatography.

Utility

The method provided herein is suitable for preparing any of a number of PEG-conjugates, and is particularly advantageous for preparing conjugates having PEG covalently attached to a single reactive site in a molecule having more than one such reactive site, while avoiding multiple protection/deprotection steps, low yields, and minimizing undesired side reactions. The synthesis method provided herein is extremely efficient, and is well-suited for adaptation to large scale production.

In addition, an exemplary 4-arm PEG-glycine-docetaxel conjugate formed in accordance with the method provided herein has been shown to be particularly useful as an anticancer agent. See, for example, Examples 3, 4 and 5. Such illustrative conjugate is effective in significantly reducing the growth of certain solid tumors as evidenced by representative lung, prostate, and breast cancer in-vivo studies in mice.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXAMPLES

The practice of the invention will employ, unless otherwise indicated, conventional techniques of organic synthesis and the like, which are within the level of skill of the art. Such techniques are fully described in the literature if not set forth in detail herein. Reagents and materials are commercially available unless specifically stated to the contrary. See, for example, J. March, Advanced Organic Chemistry: Reactions Mechanisms and Structure, 4th Ed. (New York: Wiley-Interscience, 1992), supra, and Comprehensive Organic Functional Group Transformations II, Volumes 1-7, Second Ed.: A Comprehensive Review of the Synthetic Literature 1995-2003 (Organic Chemistry Series), Eds. Katritsky, A. R., et al., Elsevier Science.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level.

Although other abbreviations known by one having ordinary skill in the art will be referenced, other reagents and materials will be used, and other methods known by one having ordinary skill in the art will be used, the following list and methods description is provided for the sake of convenience.

ABBREVIATIONS

CM carboxymethyl or carboxymethylene (—CH$_2$COOH)
DCC 1,3-dicyclohexylcarbodiimide
DCM methylene chloride
DIC N,N'-diisopropylcarbodiimide
DPTS 4-(dimethylamino)-pyridinium-p-toluenesulfonate
DMF dimethylformamide
DMAP 4-(N,N-dimethylamino)pyridine
DMSO dimethyl sulfoxide
DI deionized
HCl hydrochloric acid
HOBT hydroxybenzyltriazole
HPLC high performance liquid chromatography
IPA isopropyl alcohol
K or kDa kilodaltons
MALDI-TOF Matrix Assisted Laser Desorption Ionization Time-of-Flight
MeOH methanol
MW molecular weight
NMR nuclear magnetic resonance
RT room temperature
SCM succinimidylcarboxymethyl (—CH$_2$—COO—N-succinimidyl)
SDS-PAGE sodium dodecyl sulfate-polyacrylamide gel electrophoresis
SEC size exclusion chromatography
TFA trifluoroacetic acid
THF tetrahydrofuran
TLC thin layer chromatography
Materials and Methods.

Docetaxel (Taxotere®) was purchased from Hangzhou HETD Pharm & Chem. Co., Ltd, CHINA.

4-Arm-PEG$_{20K}$-CM and 4-arm-PEG$_{20K}$-SCM were prepared from 4-arm-PEG$_{20K}$-OH (Nektar, Huntsville, Ala.).

Sources of the following reagents were as follows: Glycine tert-butyl ester (98%, Aldrich); 4-dimethylaminopyridine (DMAP, 99%, Aldrich); N,N'-diisopropylcarbodiimide (DIC, 99%, Acros), N,N'-dicyclohexylcarbodiimide (DCC, 99%, Acros), N,N-diisopropylethylamine (DIPEA, 99%, Aldrich), and p-toluenesulfonic acid (PTSA, 98.5%, Aldrich), and all reagents were used as received. Solvents were dried before use.

DPTS: p-Toluenesulfonic acid was dried by azeotropic distillation of a benzene solution, followed by addition of an equimolar solution of DMAP in benzene. The resulting suspension was cooled to room temperature and the solid collected by suction filtration.

4-Arm-PEG$_{20K}$-glycine possesses the following structure:

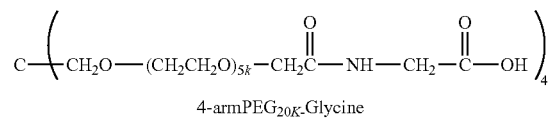

4-armPEG$_{20K}$-Glycine

All $^1$HNMR data was generated by a 300 or 400 MHz NMR spectrometer manufactured by Bruker.

Example 1

A. Synthesis of 4-arm-PEG$_{20K}$-glycine-docetaxel: DMAP-DCC Coupling

4-Arm-PEG$_{20K}$-glycine (500 mg, 0.025 mmol) was dissolved in 10 mL methylene chloride (DCM). 4-Dimethylaminopyridine (19 mg, 0.15 mmol) and DCC (32 mg, 0.15 mmol) were added to the PEG solution with stirring. After 5 minutes, docetaxel (121 mg, 0.15 mmol) was added and the reaction mixture continued to stir for an additional 24 h at room temperature. Upon completion, the reaction mixture was precipitated in a mixed solvent system of ether/IPA (1:1). The resulting white solid was collected by suction filtration, redissolved in DCM (2 mL) and reprecipitated using a single solvent system of diethyl ether (100 mL) to give the desired product after suction filtration.

$^1$H NMR analysis showed the existence of a significant amount of N-acylurea (δ 1-2.5 ppm) byproduct. Subsequent drug release studies by HPLC revealed that about 40% of the PEG (one or more carboxylic groups of each polymer molecule) was partially converted to the N-acylurea (a common side product in a DMAP-DCC coupling reaction). Since the N-acylurea byproduct cannot be hydrolyzed back to the original PEG starting material, the product purity profile is extremely complicated. Moreover, PEG starting material is not recoverable for the portion converted to N-acylurea. No further characterization of the product mixture, i.e. structural, drug loading, release rates, was conducted.

B. Alternate Approach

Covalent Attachment of Glycine Linker to Docetaxel

In view of the low yields and difficulty in purifying the desired conjugate product from the mixture formed in Example 1A, an alternate approach to preparing the desired conjugate was explored.

Rather than direct reaction of 4-Arm-PEG$_{20K}$-glycine with docetaxel in the presence of a coupling agent, covalent attachment of glycine at the 2' position of docetaxel was explored, to then be followed by coupling to the corresponding PEG reagent to form the desired of 4-arm-PEG$_{20K}$-Glycine-Docetaxel.

One equivalent of protected Fmoc-glycine was used, in an effort to minimize modification at sites other than the 2' position. Reaction conditions are shown in the reaction scheme below.

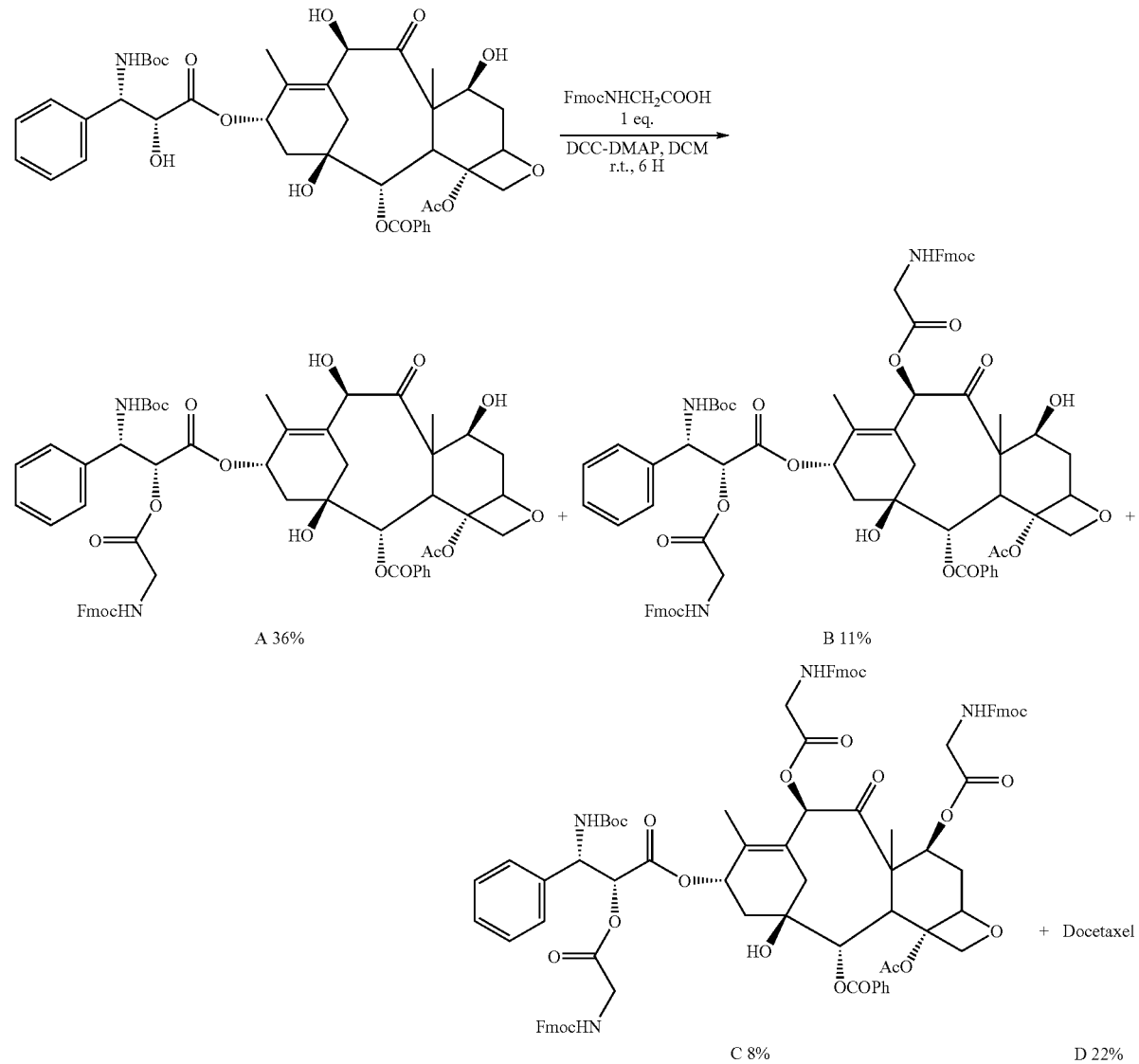

Following purification on a silica gel column, the yield of the desired conjugate (A) was only 20%. Due to the low yield of the 2'-modified docetaxel and multiple reaction products formed, further transformation to 4-arm-PEG$_{20k}$-Glycine-Docetaxel was not carried out.

Example 2

Synthesis of 4-arm-PEG$_{20K}$-Glycine-Docetaxel

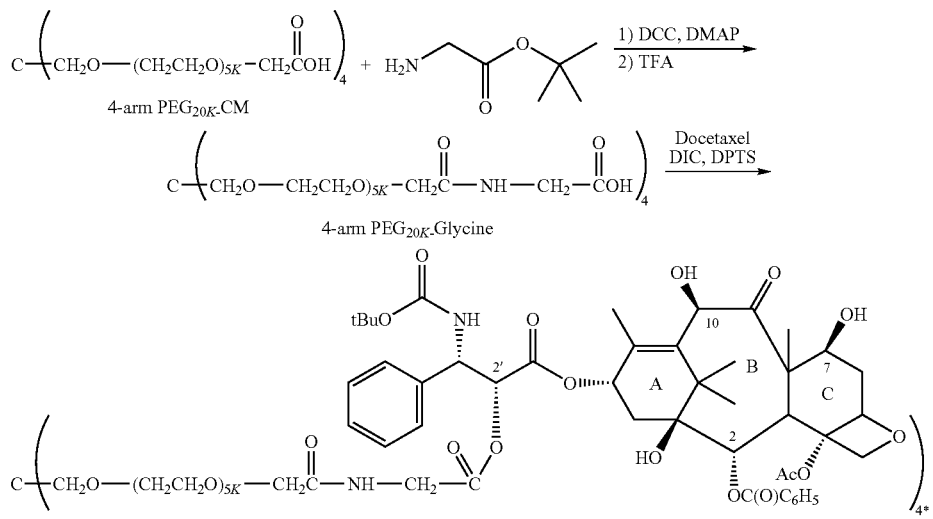

The overall synthesis of 4-arm PEG$_{20K}$-glycine docetaxel is shown in the scheme above. The "4*" represents the theoretical number of docetaxel molecules per 4-armed polymer assuming complete drug loading.

A. Preparation of 4-arm-PEG$_{20K}$-glycine t-butyl ester

4-Arm-PEG$_{20K}$-CM (12.5 g, 0.625 mmol) was dissolved in 100 mL DCM. 4-Dimethylaminopyridine (610 mg, 5.00 mmol) and DCC (625 mg, 3.00 mmol) were then added to the solution with stirring. After stirring for 5 minutes, glycine t-butyl ester.HCl (503 mg, 3.00 mmol) was added and the mixture continued to stir overnight at room temperature. Upon completion, the reaction mixture was precipitated using a mixed solvent system of ether/IPA (1:1) to give the desired 4-arm-PEG$_{20K}$-glycine t-butyl ester product (10.5 g, 0.525 mmol, yield 84%) after suction filtration.

$^{1}$H NMR (CDCl$_3$) δ 4.11 (d, 8H), 4.05 (s, 8H), 3.90-3.37 (m, ~1900H), 1.48 (s, 36H).

B. Deprotection of 4-arm-PEG$_{20K}$-glycine t-butyl ester to form 4-arm-PEG$_{20K}$-glycine 4-arm-PEG$_{20K}$-glycine t-butyl ester was deprotected using trifluoroacetic acid/methylene chloride (TFA/DCM, 3:1) and stirring at room temperature for 3 h. The product was precipitated by addition of ether (600 mL) to the reaction mixture giving the desired 4-arm-PEG$_{20K}$-glycine (9.2 g) after suction filtration.

$^{1}$H NMR (CDCl$_3$) δ 4.11 (d, 8H), 4.05 (s, 8H), 3.90-3.37 (m, ~1900H).

C. Preparation of 4-arm-PEG$_{20K}$-glycine-docetaxel

Docetaxel (776 mg, 0.96 mmol) and 4-arm-PEG$_{20K}$-glycine (4.0 g, 0.2 mmol) were dissolved in 50 mL DCM, and then freshly prepared DPTS (155 mg, 0.53 mmol), (Jeffrey S. Moore and Samuel I. Stupp, Macromolecules, 1990, 23, 65-70) and DIC (404 mg, 3.2 mmol) were added with stirring.

The reaction mixture continued to stir for 24 h at room temperature. The reaction mixture was precipitated using a mixed solvent system of ether/IPA (1:1). The resulting white solid was collected by suction filtration, redissolved in 5 ml of DCM, and reprecipitated using a single solvent system of ether (300 mL) to give the desired 4-arm-PEG$_{20K}$-glycine-docetaxel after suction filtration. Yield (Step C.) 90%.

$^{1}$H NMR (CDCl$_3$) δ 8.12 (d, 8H), 7.73 (m, 4H), 7.61 (m, 4H), 7.52 (m, 8H), 7.41 (m, 8H), 7.33 (m, 8H), 6.20 (t, 4H), 5.69 (m, 8H), 5.60 (m, 4H), 5.36 (s, 4H), 5.22 (m, 4H), 4.97 (d, 4H), 4.33 (m, 8H), 4.30 (m, 12H), 4.06 (d, 8H), 3.98 (s, 8H), 3.90-3.24 (m, ~1900H), 2.60 (m, 4H), 2.36 (m, 20H), 1.96 (s, 12H), 1.86 (m, 8H), 1.75 (s, 12H), 1.68 (m, 8H), 1.35 (s, 36H), 1.25 (s, 12H), 1.13 (s, 12H). All chemical shift values in ppm (ε).

D. Drug loading and Hydrolysis of 4-arm-PEG$_{20K}$-glycine-docetaxel

Drug loading was determined $^{1}$H NMR (8%) and RP-HPLC (6.2%) analytical methods while hydrolysis rates (in phosphate buffer) were determined exclusively by RP-HPLC.

Calculation of the Drug Loading by $^{1}$H NMR:

Samples of different PEG-docetaxel concentrations were prepared, and the number of scans was then varied depending on the concentration of the sample. Based on the averaged proton peak integration of all spectra obtained, the drug loading was determined.

Calculation of the Drug Loading and Hydrolysis Rate by HPLC

Instrument: HP 1100
Column: C$_{18}$ column
Mobile Phase: A: 0.1% TFA in H$_2$O; B: Acetonitrile
Flow Rate: 0.5 mL/min
Gradient Table:

| Time (min) | A % | B % |
|---|---|---|
| 0 | 60% | 40% |
| 15 | 0 | 90% |

Drug Loading Determination: Drug loading and hydrolysis rates were determined experimentally as follows: Using the abovementioned HPLC method, 10.8 mg docetaxel was dissolved in a mixed solvent system of acetonitrile/PBS (1:1, 10 mL, pH 7.4). This stock solution was further diluted serially to give the following concentrations of docetaxel solutions: 540 µg/mL, 405 µg/mL, 300 µg/mL, 216 µg/mL, 108 µg/mL and 54 µg/mL. The peak areas were obtained for each concentration and a standard curve was generated. Then 30.4 mg of 4-arm-PEG$_{20K}$-docetaxel was dissolved in 10 mL PBS, pH 7.4. The solution was filtered, and then aliquots of 0.3 mL were placed into 10 individual HPLC vials. These vials were stored at 37° C. and prior to use, 0.3 mL of acetonitrile was added to ensure all PEG-docetaxel and free docetaxel present in the sample were dissolved. One vial was used for each injection, and injections were made at various timepoints over a course of 200 h (8.3 d). The appearance of free drug released from the PEG-conjugate was monitored and upon completion the final concentration was determined against the standard curve.

The drug loading value refers to the average number of docetaxel molecules covalently attached to the polymer in the 4-arm-PEG$_{20K}$-glycine-docetaxel product. The calculated molecular weight of the 4-arm PEG$_{20K}$-glycine-docetaxel product, assuming 4 docetaxel molecules per 4-arm polymer, is approximately 23,232. The molecular weight of docetaxel is 808. Assuming complete drug loading (4 docetaxels per polymer), the theoretical percent weight of drug contained in the product is (3232/23232)100 or 13.9%. The actual observed weight of drug, as determined by HPLC, was 6.2%, which corresponds to an average number of docetaxels per polymer of 1.78. The drug loading value determined by $^1$H NMR was 8%, which corresponds to an average number of docetaxel molecules per polymer of about 2.3. Thus, for this preparation, based upon the average of both methods, the average number of docetaxel molecules per polymer is slightly higher than 2.00.

Half-life Determination. The determination of hydrolysis rate, reported as a half-life, utilized the same analytical method outlined above for the drug loading. Once the drug release was complete, the half-life was calculated by either determining the time at which the concentration (area %) of the free drug equaled 50% or, if perfectly linear, by determining the slope of the plot (ln 1-S % vs. hour) and using the following equation:

Half-life=ln(2)/slope

The half life for 4-arm-PEG$_{20K}$-Docetaxel was determined to be 15.3 h.

Example 3

Anti-tumor Activity of 4-arm-PEG$_{20K}$-glycine-docetaxel in Mice Implanted with NCI-H460 Lung Tumors Human NCI-H460 lung tumors (30 to 40 fragments of each) were implanted subcutaneously in the mice (Charles Rivers Labs: NCr nu/nu) near the right axillary area. The day of implantation was designated Day 0 and the tumors were allowed to reach a weight of 100-245 mg in weight prior to treatment.

The animals were randomized into groups in a manner such that the median tumor weights on the first day of treatment were as close to each other as possible.

Treatment: The mice received 1 or 2 intravenous doses of test compound or vehicle (saline).

Tumor measurement: The animals were weighed and the tumors measured twice weekly after administration of the first injection. The tumor volume was measured by caliper measurements (mm) and using the formula of an ellipsoid sphere: L×W$^2$/2=mm$^3$, where L and W refer to the larger and smaller perpendicular dimensions collected at each measurement. This formula was also used to calculate tumor weight assuming unit density (1 mm$^3$=1 mg).

Study Duration: Any animal found moribund or any animal whose tumor reached 4000 mg, ulcerated or was sloughed off was euthanized prior to study termination.

Figure 2:
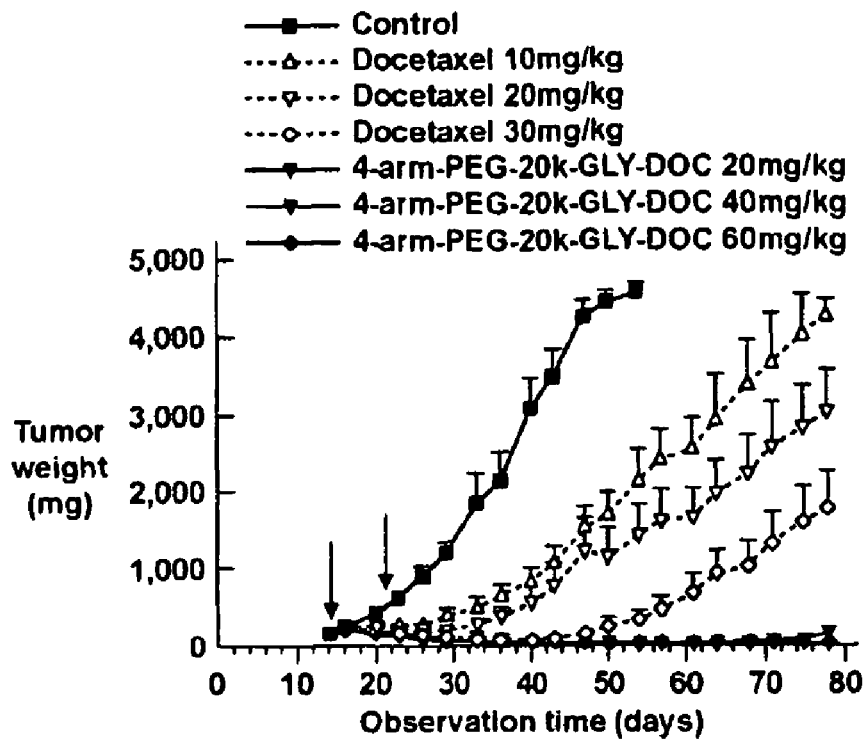
FIG. 2 is a plot demonstrating the effects of two doses of each of three different dosage amounts of docetaxel (10 mg/kg, 20 mg/kg, and 30 mg/kg) and 4-arm-PEG$_{20k}$-glycine-docetaxel (20 mg/kg, 40 mg/kg, and 60 mg/kg) in female xenograft athymic nude mice implanted with DU-145 prostate tumors over time as described in Example 4.
Figure 3:
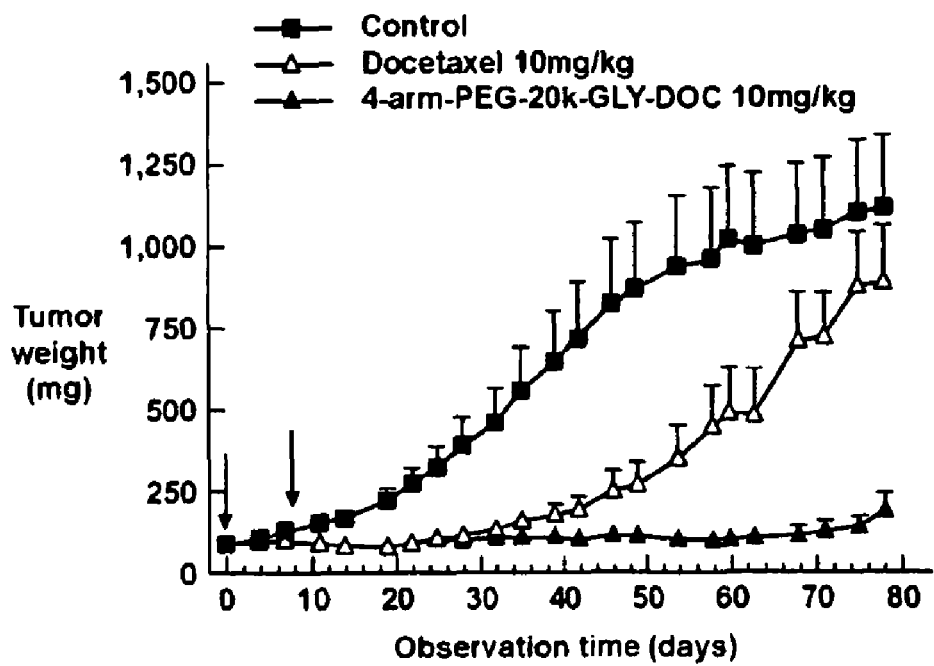
FIG. 3 is a plot demonstrating the anti-tumor effect of docetaxel and 4-arm-PEG$_{20k}$-glycine-docetaxel, respectively, over time in mice implanted with MCF-7 breast tumors as described in Example 5.

Results. Two different efficacy studies were conducted. The 1$^{st}$ study evaluated the efficacy of 4-arm-PEG$_{20K}$-Docetaxel and docetaxel against H460 NSCLC tumors. FIGS. 1-3 illustrate the effect of a single dose of each compound on the tumor growth. It was observed that doses of 20 and 40 mg/kg of the PEGylated docetaxel provided an improved anti-tumor effect over the un-PEGylated free compound. The 10 mg/kg dose showed a significant difference between the two compounds.

In the 2$^{nd}$ study, the anti-tumor efficacy (H460 NSCLC tumors) was measured up to the maximum tolerated dose for athymic nude mice. The animals tolerated docetaxel up to 30 mg/kg and PEG-docetaxel up to 60 mg/kg. FIG. 1 illustrates the effect of two doses (q7d×2) of each compound on the tumor growth. It is again evident from the results, that the PEGylated compound provided an improved anti-tumor effect over the Docetaxel compound. A dose response is clearly evident among the three PEGylated drug doses when compared to the three un-PEGylated drug doses.

Example 4

Anti-tumor Activity of 4-arm-PEG$_{20K}$-glycine-docetaxel in Mice Implanted with DU-145 Prostate Tumors The study was carried out as described in Example 3 above, with the exception that the tumors used were DU-145 prostate tumors.

The anti-tumor efficacy was evaluated against prostate tumors (DU-145) up to the maximum tolerated dose of each compound. The animals tolerated docetaxel up to 30 mg/kg and PEG-docetaxel up to 60 mg/kg.

FIG. 2 illustrates the anti-tumor effect of two doses (q7d×2) of each compound. It is again evident from the results that the PEGylated compounds completely suppressed the tumor growth at all 3 doses tested and for the 78 day observation period. The docetaxel compound showed good activity, but the tumors did recover and grow after 30-50 days.

Example 5

Anti-tumor Activity of 4-arm-PEG$_{20K}$-glycine-docetaxel in Mice Implanted with MCF-7 Breast Tumors Up to 100 mice (Charles Rivers Labs: CD-1 Fox nI nu) were surgically implanted in the lateral side of the neck with a subcutaneous 17 β-estradiol (estrogen) pellet (1.00 mg/pellet; Innovative Research of America, Sarasota, Fla., USA) at least 2 days prior to cell inoculation. These pellets release estrogen at a rate of 0.011 mg/day for 90 days after implant. Following surgery, approximately 1×10$^6$ MCF-7 cells in a volume of 0.1 mL phosphate buffered saline (PBS)/Matrigel™ (1:1 v/v) were injected subcutaneously in the right flank. The tumors were allowed to reach a range of 50-150 mm$^3$. Day 0 for this study corresponded to the first day of dosing.

The animals were randomized into groups in a manner such that the median tumor weights on the first day of treatment were as close to each other as possible.

Treatment: The mice received 1 or 2 intravenous doses of test compound or vehicle (saline).

Tumor measurement: The animals were weighed and the tumors measured twice weekly after administration of the first injection. The tumor volume was measured by caliper measurements (mm) and using the formula of an ellipsoid sphere: $L \times W^2/2 = mm^3$, where L and W refer to the larger and smaller perpendicular dimensions collected at each measurement. This formula was also used to calculate tumor weight assuming unit density (1 $mm^3$=1 mg).

Study Duration: Any animal found moribund or any animal whose tumor reached 1500 cc, ulcerated or was sloughed off was euthanized prior to study termination.

Results: The anti-tumor efficacy was evaluated against breast tumors (MCF-7) at doses of 10, 20 and 30 mg/kg. The results showed complete suppression of tumor growth at the two high doses and for both compounds tested. FIG. 3 illustrates the anti-tumor effect of the 10 mg/kg dose (q7d×2).

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for covalently attaching a polyethylene glycol polymer to docetaxel, said method comprising the step of:
reacting docetaxel with a polyethylene glycol comprising a functional group reactive with a hydroxyl group within docetaxel in the presence of a coupling reagent and 4-(dimethylamino)-pyridinium-p-toluenesulfonate (DPTS), under conditions effective to promote reaction between said docetaxel and said polyethylene glycol to thereby form a polyethylene glycol docetaxel conjugate having a single polyethylene glycol covalently attached, via an ester linkage, to the hydroxyl group within docetaxel.

2. The method of claim 1, wherein said coupling reagent is a carbodiimide.

3. The method of claim 2, wherein said coupling reagent is selected from the group consisting of dicyclohexylcarbodiimide (DCC), N,N'-diisopropylcarbodiimide (DIC), 1-(3-dimethylaminopropyl)-3-ethylcarbodiimide hydrochloride (EDAC), 1-(3-dimethylaminopropyl)-3-ethylcarbodiimide (EDC), N-tert-butyl-N'-m ethylcarbodiimide (TBMC), and N-tert-butyl-N'-ethylcarbodiimide (TBEC).

4. The method of claim 1, wherein said coupling reagent is N,N'-diisopropylcarbodiimide.

5. The method of claim 1, wherein said reacting step is carried out in an organic solvent selected from the group consisting of dichloromethane, chloroform, acetonitrile, and tetrahydrofuran.

6. The method of claim 5, wherein said reacting step is carried out at a temperature ranging from 0° C. to 100° C.

7. The method of claim 6, wherein said reacting step is carried out at room temperature.

8. The method of claim 1, wherein the amount of DPTS in said reacting step ranges from about 0.05 to 0.75 equivalents relative to said hydroxyl group within docetaxel.

9. The method of claim 8, wherein the amount of DPTS in said reacting step ranges from about 0.10 to 0.60 equivalents relative to said hydroxyl group within docetaxel.

10. The method of claim 1, wherein the amount of said coupling reagent ranges from about 1.25 to 5 equivalents relative to said hydroxyl group within docetaxel.

11. The method of claim 1, wherein said second functional group is carboxyl.

12. The method of claim 1, wherein said single hydroxyl group within docetaxel is the 2'-hydroxyl group of docetaxel.

13. The method of claim 1, wherein said polyethylene glycol is selected from the group consisting of linear, branched, forked, and multi-armed polyethylene glycol.

14. The method of claim 13, wherein said polyethylene glycol comprises from 3 to 25 arms.

15. The method of claim 14, wherein said polyethylene glycol comprises a number of arms selected from 3, 4, 5, 6, 7, 8, 9, and 10.

16. The method of claim 15, wherein said polyethylene glycol comprises a polyol or a polyamine core.

17. The method of claim 16, wherein said polyethylene glycol comprises a polyol core selected from glycerol, trimethylolpropane, sorbitol, hexaglycerol, and pentaerythritol.

18. The method of claim 1, wherein said polyethylene glycol comprises from 1 to about 10 of said second functional groups.

19. The method of claim 18, wherein said polyethylene glycol comprises a number of said second functional groups selected from 1, 2, 3, 4, 5, and 6.

20. The method of claim 19, wherein said polyethylene glycol comprises a structure selected from:

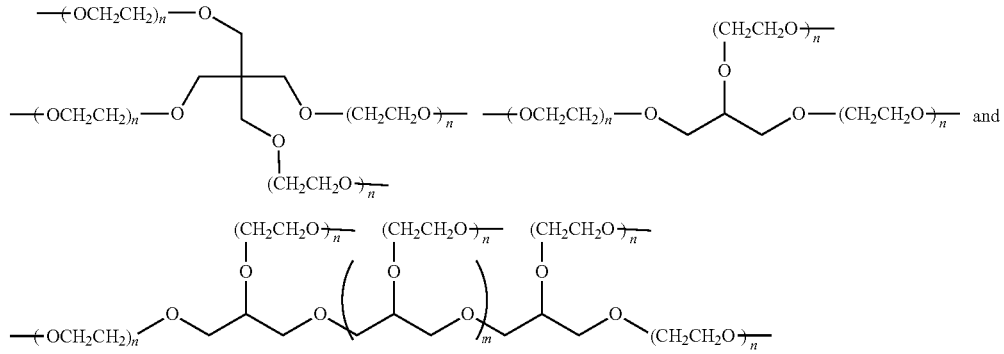

wherein
n ranges from about 5 to about 400,
m ranges from 0 to 5, and
the total molecular weight of the multi-arm polymer ranges from about 1500 to about 60,000 daltons.

21. The method of claim 20, said method lacking a protection step.

22. The method of claim 21, wherein said polyethylene glycol is:

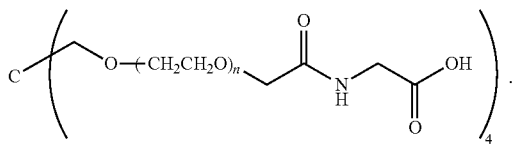

23. The method of claim 22, wherein said reacting step forms a conjugate having docetaxel covalently attached to said polyethylene glycol at only its 2' position.

24. The method of claim 23, wherein said reacting step forms a conjugate possessing an average number of docetaxel molecules per polyethylene glycol ranging from about 2.1 to 3.75.

25. The method of claim 24, wherein said reacting step forms a conjugate possessing an average number of docetaxel molecules per polyethylene glycol ranging from about 2.3 to 3.2.

* * * * *